United States Patent
Minekus

(10) Patent No.: US 10,417,938 B2
(45) Date of Patent: Sep. 17, 2019

(54) DIGESTION SYSTEM

(75) Inventor: Mans Minekus, Delft (NL)

(73) Assignee: Triskelion B.V., Zeist (NL)

( * ) Notice: Subject to any disclaimer, the term of this patent is extended or adjusted under 35 U.S.C. 154(b) by 110 days.

(21) Appl. No.: 14/123,319

(22) PCT Filed: May 31, 2012

(86) PCT No.: PCT/NL2012/050383
§ 371 (c)(1),
(2), (4) Date: Jan. 24, 2014

(87) PCT Pub. No.: WO2012/165962
PCT Pub. Date: Dec. 6, 2012

(65) Prior Publication Data
US 2014/0329216 A1 Nov. 6, 2014

(30) Foreign Application Priority Data
May 31, 2011 (EP) .................... 11168291

(51) Int. Cl.
G09B 23/30 (2006.01)
B01D 61/14 (2006.01)
G01N 13/00 (2006.01)
B01D 63/02 (2006.01)

(52) U.S. Cl.
CPC .......... *G09B 23/30* (2013.01); *B01D 61/147* (2013.01); *B01D 63/02* (2013.01); *G01N 13/00* (2013.01); *G09B 23/303* (2013.01); *B01D 2313/90* (2013.01); *G01N 2013/006* (2013.01)

(58) Field of Classification Search
CPC ........ G01N 13/00; G01N 33/15; G09B 23/30; G09B 23/303; B01D 63/02; B01D 61/147; B01D 2313/90
See application file for complete search history.

(56) References Cited

U.S. PATENT DOCUMENTS

| | | | |
|---|---|---|---|
| 4,335,438 A | 6/1982 | Smolen | |
| 5,187,010 A | 2/1993 | Parham et al. | |
| 6,022,733 A * | 2/2000 | Tam | C12M 25/10 435/287.1 |

(Continued)

FOREIGN PATENT DOCUMENTS

| | | |
|---|---|---|
| CN | 2059360 U * | 7/1990 |
| CN | 1356923 A | 7/2002 |

(Continued)

OTHER PUBLICATIONS

H2O engineering, Microfiltraton, <http://www.h2oengineering.com/technologies/membrane-micro-filtration/>, Jun. 17, 2008.*

(Continued)

*Primary Examiner* — Krishnan S Menon
*Assistant Examiner* — Waqaas Ali
(74) *Attorney, Agent, or Firm* — Banner & Witcoff, Ltd.

(57) ABSTRACT

The invention relates to a digestion system for analyzing the intestinal fluid. The system comprises a compartment containing the fluid content and a micro filter for filtering particles in the fluid content having a size beyond the micro range. The system further comprises a pertractor arranged downstream to the micro filter for removing digested lipophilic particles.

13 Claims, 1 Drawing Sheet

(56) References Cited

U.S. PATENT DOCUMENTS

Figure 1:
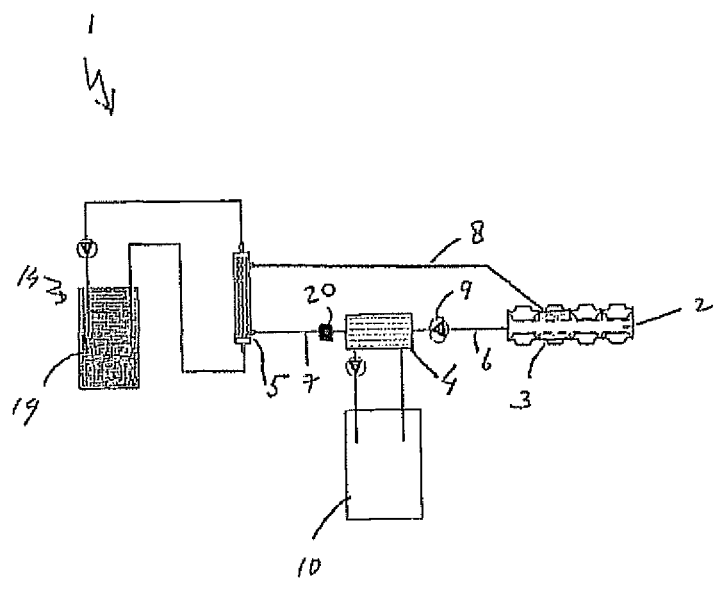

| | | | |
|---|---|---|---|
| 6,793,825 B2 | 9/2004 | Maass et al. | |
| 6,929,782 B1 | 8/2005 | Ciliberto et al. | |
| 6,969,466 B1 * | 11/2005 | Starner | B01J 39/043 |
| | | | 210/663 |
| 2003/0088369 A1 | 5/2003 | Hughes | |
| 2007/0039887 A1 * | 2/2007 | Bomberger | A61M 1/34 |
| | | | 210/644 |
| 2009/0064768 A1 | 3/2009 | Alkhawam et al. | |
| 2011/0060273 A1 * | 3/2011 | Ofsthun | A61M 1/1696 |
| | | | 604/29 |
| 2015/0157781 A1 | 6/2015 | Kyle et al. | |

FOREIGN PATENT DOCUMENTS

| | | | | |
|---|---|---|---|---|
| CN | 101314501 A | 12/2008 | | |
| CN | 101801431 A | 8/2010 | | |
| EP | 0642382 A1 | 3/1995 | | |
| EP | 0862943 A1 * | 9/1998 | | B01D 63/04 |
| EP | 1907108 A1 | 4/2008 | | |
| EP | 2182342 A1 | 5/2010 | | |

OTHER PUBLICATIONS

International Search Report—PCT/NL2012/050383—dated Aug. 8, 2012.

* cited by examiner

DIGESTION SYSTEM

CROSS-REFERENCE TO RELATED APPLICATIONS

This application is a U.S. National Stage application under 35 U.S.C. § 371 of International Application PCT/NL2012/050383 (published as WO 2012/165962 A1), filed May 31, 2012, which claims priority to Application EP 11168291.0, filed May 31, 2011. Benefit of the filing date of each of these prior applications is hereby claimed. Each of these prior applications is hereby incorporated by reference in its entirety.

The invention relates to a digestion system.

For the purpose of analyzing digestion processes in the human stomach and intestine, it is desired to provide accurate simulating models.

In known digestion systems, a micro filter is used for filtering micelles that contain digested lipids and other lipophilic compounds such as drugs, while undigested fat droplets are retained in the simulated intestinal content. However, the micro filter also passes digested water soluble particles, such as enzymes, bile and food particles.

According to an aspect of the invention, there is provided a digestion system for analyzing the intestinal fluid, comprising a compartment containing the fluid content and a micro filter for filtering particles in the intestinal content having a size beyond the micro range, further comprising a pertractor arranged downstream to the micro filter for removing digested lipophilic particles, wherein the pertractor includes a container and a plurality of hollow fiber membranes arranged in the container, further including an organic solvent providing module for flowing organic solvent through the hollow fiber membranes, wherein the container is provided with an input port for receiving fluid filtered by the micro filter, and wherein the system further includes an ultra filter arranged downstream to the micro filter for removing digested water soluble particles.

By applying a pertractor for removing digested lipophilic particles, the behaviour of lipophilic particles in the intestinal content can advantageously be studied more accurately, e.g. for determining the availability of lipophilic particles for absorption through the intestinal wall.

The invention is also directed to a method for analyzing the intestinal fluid.

Figure 2:
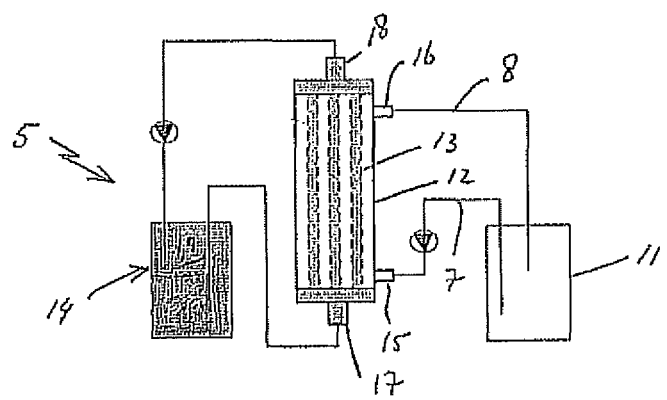

By way of example only, embodiments of the present invention will now be described with reference to the accompanying figures in which FIG. 1 shows a schematic scheme of a digestion system according to the invention, and FIG. 2 shows a schematic scheme of the pertractor included in the digestion system of FIG. 1.

The figures are merely schematic views of preferred embodiments according to the invention. In the figures, the same reference numbers refer to equal or corresponding parts.

FIG. 1 shows a schematic scheme of a digestion system 1 according to the invention. The system 1 is arranged for analyzing the intestinal fluid. The system 1 comprises a compartment 2 containing the fluid content and a micro filter 3 for filtering particles in the fluid content having a size beyond the micro range, i.e. beyond circa 10 micron. The micro filter 3 retains fat particles but passes digested lipophilic particles and digested water soluble particles. Further, the system 1 comprises an ultra filter 4 and a pertractor 5, both arranged downstream to the micro filter 3.

The ultra filter 4 is arranged for removing digested water soluble particles, while the pertractor 5 is arranged for removing digested lipophilic particles. In the shown embodiment, the ultra filter 4 is located upstream to the pertractor 5. However, the ultra filter 4 could also be located downstream to the pertractor 5.

The system 1 further includes a multiple number of flow paths for forming a serial chain of tools processing the fluid in the compartment 2. In the shown embodiment, a first flow path 6 connects the micro filter 3 to the ultra filter 4, and a second flow path 7 connects the ultra filter 4 to the pertractor 5. Further, a third flow path 8 connects the pertractor 5 back to the compartment 2, forming a closed loop. The system 1 includes a device, e.g. a pump 9 for forcing a fluid flow in a clockwise manner through the loop. By providing a loop, the process of removing particles from the content of the compartment 2 can be repeated again and again, each time improving the filter result.

In this context it is noted that the third flow path 8 implementing a feedback path for flowing a residue back to the compartment, is optional. It is further noted, that the system 1 can also be constructed without the ultra filter 4. Then, the pertractor 5 can be arranged directly downstream to the micro filter 3.

The ultra filter 4 can be implemented as a dialysis apparatus including a dialysate device 10 for filtering digested water soluble particles from the fluid.

FIG. 2 shows a schematic scheme of the pertractor 5. The second flow path 7 flows the fluid towards the pertractor 5 while the third flow path 8 flows the fluid from the pertractor 5. In FIG. 2 an additional container 11 is shown indicating that the fluid in the flow paths 7, 8 is in the water phase.

The pertractor 5 includes a container 12 and a plurality of hollow fiber membranes 13 arranged in the container 12. The pertractor 5 also includes an organic solvent providing module 14 for flowing organic solvent through the hollow fiber membranes 13.

The container 12 is provided with an input port 15 for receiving fluid flowing through the second flow path 8. The container 12 is further provided with an output port 16 for flowing fluid that enters the container via the input port 15, towards the third flow path 8. The container 12 also includes an organic solvent input port 17 and an organic solvent output port 18 so that the organic solvent can flow from a reservoir 19 of the organic solvent providing module 14 into the hollow fiber membranes 13, and back to the reservoir 19.

The pertractor 5 is arranged such that the fluid entering via the input port 15 flow along the hollow fiber membranes 13 and leave the container 12 via the output port 16.

During operation of the system 1, the water phase and the organic solvent flow, e.g. heptane, contact each other without mixing since the membranes are hydrophobic. During the contact phase, digested lipophilic particles move from the water phase to the organic solvent phase. In this way, digested lipophilic particles can selectively transfer to the organic solvent phase. Due to the large contact area of the water phase and the organic solvent, the selective filtering step of filtering digested lipophilic particles, such as micelles and drugs particles, can be performed relatively quickly.

Optionally, the system may include a conditioner 20 arranged upstream to the pertractor 5 for lowering the pH value of the fluid content, e.g. towards a pH value of circa 5.

The invention is not restricted to the embodiments described herein. It will be understood that many variants are possible.

Other such variants will be apparent for the person skilled in the art and are considered to fall within the scope of the invention as defined in the following claims.

The invention claimed is:

1. A digestion system for analyzing intestinal fluid, comprising a compartment for containing the fluid content and a micro filter for filtering particles in the fluid content having a size beyond the micro range, wherein the micro filter is formed integrally with the compartment, the system further comprising a pertractor arranged downstream to the micro filter for removing digested lipophilic particles, wherein the pertractor includes a container and a plurality of hollow fiber membranes arranged in the container, further including an organic solvent providing module for flowing organic solvent through the hollow fiber membranes, wherein the container is provided with an input port for receiving fluid filtered by the micro filter, the system further comprising an ultra filter arranged downstream to the micro filter for removing digested water soluble particles, and a feedback path for flowing fluid received from either the ultra filter or the pertractor back to the compartment.

2. A digestion system according to claim 1, wherein the pertractor is configured to flow fluid that enters the container via the input port, along the hollow fiber membranes.

3. A digestion system according to claim 1, wherein the container is further provided with an output port for flowing fluid that enters the container via the input port.

4. A digestion system according to claim 1, further including a conditioner arranged upstream to the pertractor for lowering a pH value of the fluid content.

5. A digestion system according to claim 1, wherein the ultra filter is arranged either downstream or upstream to the pertractor.

6. A digestion system according to claim 2, wherein the container is further provided with an output port for flowing fluid that enters the container via the input port.

7. A digestion system for analyzing intestinal fluid, comprising a compartment for containing the fluid content and a micro filter for filtering particles in the fluid content having a size beyond the micro range, wherein the micro filter is formed integrally with the compartment, the system further comprising a pertractor arranged downstream to the micro filter for removing digested lipophilic particles, wherein the pertractor includes a container and a plurality of hollow fiber membranes arranged in the container, further including an organic solvent providing module for flowing organic solvent through the hollow fiber membranes, wherein the container is provided with an input port for receiving fluid filtered by the micro filter, wherein the system further includes an ultra filter arranged downstream to the micro filter for removing digested water soluble particles, and wherein the compartment is in fluid communication, through a feedback path, with either the ultra filter or the pertractor.

8. A digestion system for analyzing intestinal fluid, comprising a compartment for containing the fluid content and a micro filter for filtering particles in the fluid content having a size beyond the micro range, further comprising a pertractor arranged downstream to the micro filter for removing digested lipophilic particles, wherein the pertractor includes a container and a plurality of hydrophobic hollow fiber membranes arranged in the container, further including an organic solvent providing module for flowing organic solvent through the hollow fiber membranes, wherein the container is provided with an input port for receiving fluid filtered by the micro filter, the system further comprising an ultra filter arranged downstream to the micro filter for removing digested water soluble particles, and a feedback path for flowing fluid received from either the ultra filter or the pertractor back to the compartment.

9. The digestion system of claim 8, wherein the pertractor is configured to flow fluid that enters the container via the input port, along the hollow fiber membranes.

10. The digestion system of claim 8, wherein the container is further provided with an output port for flowing fluid that enters the container via the input port.

11. The digestion system of claim 8, further including a conditioner positioned upstream of the pertractor for lowering a pH value of the fluid content.

12. The digestion system of claim 8, wherein the ultra filter is positioned either downstream or upstream to the pertractor.

13. The digestion system of claim 8, wherein the micro filter is formed integrally with the compartment.

* * * * *